United States Patent [19]
Barlow et al.

[11] 3,948,990
[45] Apr. 6, 1976

[54] CHEMICAL COMPOUNDS AND COMPOSITIONS

[75] Inventors: Charles Brian Barlow, Camberley; Brian Graham White, Crowthorne, both of England

[73] Assignee: Imperial Chemical Industries Limited, London, England

[22] Filed: Aug. 13, 1974

[21] Appl. No.: 497,055

Related U.S. Application Data

[63] Continuation of Ser. No. 230,512, Feb. 29, 1972, abandoned.

[30] Foreign Application Priority Data

Mar. 19, 1971 United Kingdom............... 7292/71
Aug. 26, 1971 United Kingdom............. 40087/71
Feb. 4, 1972 United Kingdom............... 5356/72

[52] U.S. Cl. .............. 260/576; 260/578; 260/646; 260/649 R; 260/649 F; 260/650 R; 260/650 F; 424/330
[51] Int. Cl.² .................... C07C 87/54; C07C 87/64
[58] Field of Search .................................... 260/576

[56] References Cited
UNITED STATES PATENTS
2,212,825   8/1940   Dandt et al. ................... 260/576 X FOREIGN PATENTS OR APPLICATIONS
868,165   5/1961   United Kingdom................ 260/576

*Primary Examiner*—Robert V. Hines
*Attorney, Agent, or Firm*—Cushman, Darby & Cushman

[57] ABSTRACT

Pesticidal compounds of formula I where Z represents a halo-substituted naphthyl group or a group of formula II wherein $X^1$, $X^2$, $X^3$ and $X^4$ are halogen, and Y is halogen, trifluoromethyl, nitro or alkyl:

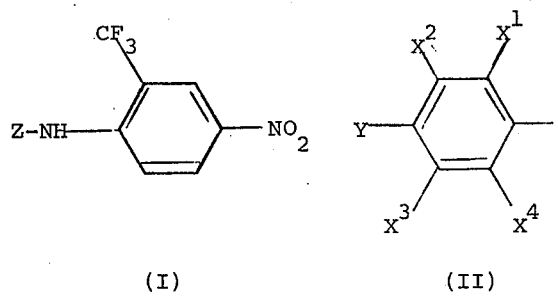

6 Claims, No Drawings

CHEMICAL COMPOUNDS AND COMPOSITIONS

This is a continuation, of application Ser. No. 230,512 filed Feb. 29, 1972 and now abandoned.

This invention relates to diphenylamine derivatives, to pesticidal compositions comprising them and to methods of combating pests using them.

In British Patent Specification Ser. No. 868,165 there are described a class of diphenylamine derivatives of the general formula:

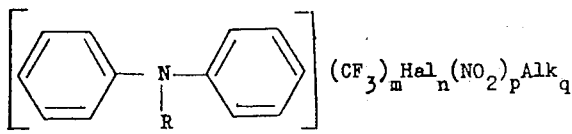

in which Hal is a fluorine, chlorine or bromine atom, Alk is an alkyl radical containing up to 4 carbon atoms, R is hydrogen or an alkyl radical containing up to 4 carbon atoms, $m$ and $p$ are whole numbers from 1 to 3, $n$ is zero or a whole number up to 6 and $q$ is zero or a whole number up to 3, $m$, $n$, $p$ and $q$ together being a whole number not exceeding 10, all the substituents apart from R being nuclear substituents.

These compounds were disclosed as having insecticidal, especially mite ovicidal, activity. All the examples disclosed possessed a 2-nitro substituent.

We have discovered that within the class of compounds defined above there is a group of compounds having very superior pesticidal activity, including broad spectrum insecticidal and fungicidal properties.

According to the present invention there are provided compounds having the formula:

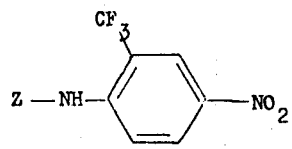

where Z represents a halo-substituted naphthyl radical or the radical having the formula:

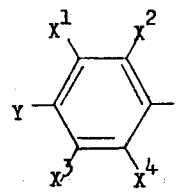

wherein $X^1$, $X^2$, $X^3$ and $X^4$, which may be the same or different, are halogen atoms, and Y is halogen, trifluoromethyl, nitro or alkyl.

In a preferred aspect the invention provides compounds having the formula:

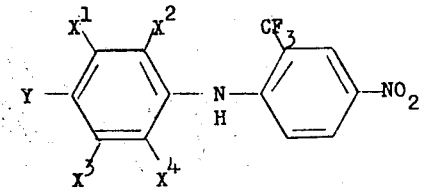

wherein $X^1$, $X^2$, $X^3$ and $X^4$, which may be the same or different, are halogen atoms, and Y is halogen, trifluoromethyl, nitro or alkyl.

In a more preferred aspect the present invention provides compounds having the formula:

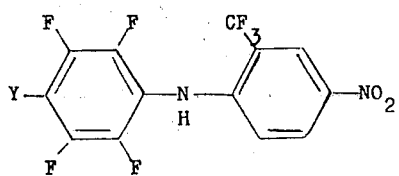

wherein Y is fluorine, trifluoromethyl, nitro, or methyl.

Specific examples according to the present invention are those whose structural formulae are given in Table I below, together with a melting point in degrees centigrade for each compound.

| Compound No: | Structural Formula: | Melting Point °C |
|---|---|---|
| 1 | ![structure] | 103–108 |
| 2 | ![structure] | 144.7–145.4 |

-continued

| Compound No: | Structural Formula: | Melting Point °C |
|---|---|---|
| 3 | 2,4-bis(trifluoromethyl)-3,5,6-trifluorophenyl bonded via NH to 2-trifluoromethyl-4-nitrophenyl | 128.5–138.5 |
| 4 | 4-bromo-2,3,5,6-tetrafluorophenyl–NH–2-trifluoromethyl-4-nitrophenyl | 110.2–111.7 |
| 5 | 2,4,6-trichloro-3,5-difluorophenyl–NH–2-trifluoromethyl-4-nitrophenyl | 134.1–134.4 |
| 6 | 4-methyl-2,3,5,6-tetrafluorophenyl–NH–2-trifluoromethyl-4-nitrophenyl | 105.9–109.3 |
| 7 | pentafluorophenyl–NH–2-trifluoromethyl-4-nitrophenyl | 65.6–67.0 |
| 8 | heptafluoro-2-naphthyl–NH–2-trifluoromethyl-4-nitrophenyl (or 1-naphthyl isomer) | 129.0–131.8 |

The compounds of the present invention may be prepared by treating 4-nitro-2-trifluoromethylaniline with a halo substituted naphthalene or with a compound of the formula:

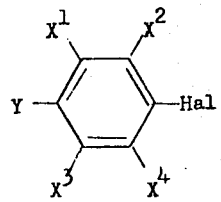

wherein Hal is an atom of halogen and X, $X^2$, $X^3$, $X^4$ and Y have any of the meanings given hereinabove. The process is facilitated by the presence of a base, for example sodium hydride, and is usually carried in the presence of a solvent or diluent, for example dimethylformamide or tetrahydrofuran.

In a preferred method 4-nitro-2-trifluoromethylaniline is treated with the base, and the product of the treatment further treated with a halo-substituted naphthalene or with the compound of formula:

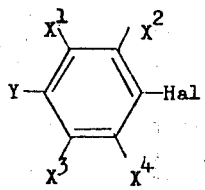

In an alternative procedure a compound of formula:

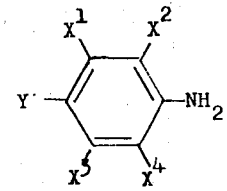

or a halo-substituted naphthylamin is treated with 2-halo-5-nitro-$\alpha,\alpha,\alpha$-trifluorotoluene, the reaction being facilitated by the presence of a base.

The compounds themselves may be used to combat pests, but they are more conveniently utilized in the form of compositions in which the active ingredient is admixed with a diluent or carrier material.

In a further aspect therefore the present invention provides pesticidal compositions comprising as an active ingredient, a compound having the formula:

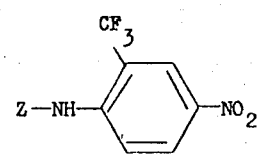

wherein Z represents a halo-substituted naphthyl radical or the radical having the formula:

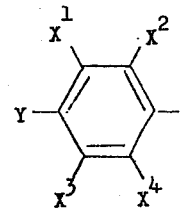

wherein $X^1$, $X^2$, $X^3$ and $X^4$, which may be the same or different, are halogen atoms, and Y is halogen, trifluoromethyl, nitro or alkyl.

In a preferred aspect the invention provides pesticidal compositions comprising as an active ingredient a compound having the formula:

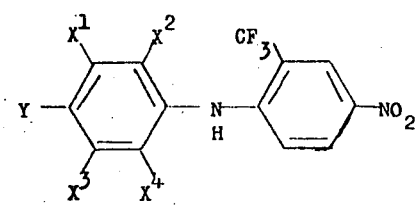

wherein $X^1$, $X^2$, $X^3$ and $X^4$, which may be the same of different, are halogen atoms, and Y is halogen, trifluoromethyl, nitro, or alkyl.

In a more preferred aspect the invention provides pesticidal compositions comprising as an active ingredient a compound being the formula:

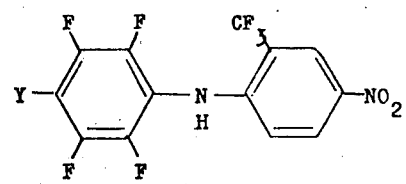

wherein Y is fluorine, trifluoromethyl, nitro or methyl.

In a yet more preferred aspect the invention provides pesticidal compositions comprising as an active ingredient any of the compouds give in Table I.

Compounds of the invention and compositions comprising them are very toxic towards insect and other invertibrate pests, including for example the following:

| | |
|---|---|
| Tetranychus telarius | (red spider mites) |
| Plutella maculipennis | (diamond back moth) |
| Aphis fabae | (black aphids) |
| pieris brassicae | (cabbage white caterpiller) |
| Blattella germanica | (cockroaches) |
| Megoura vioiae | (green aphids) |
| Phaodon cochleariae | (mustard beetle) |
| Tribolium confusum | (flour beetles) |
| Musca domestica | (houseflies) |
| Aedes aegypti | (mosquitos) |
| Agriolimax reticulatus | (greyfield slug) |
| Calandra granaria | (grain weevils) |

The compounds of the invention, and compositions comprising them, possess activity against a wide variety of plant foliar and post-harvest fungal and bacterial diseases including, for example, the following specific diseases:

| | | |
|---|---|---|
| Puccinia recondita | (rust) | on tomatoes |
| Botrytis cinerea | (chocolate spot) | on broad beans |
| Phytophthora infestans | (late blight) | on broad beans |
| Podosphaera leucotricha | (powdery mildew) | on apple |
| Uncinula necator | (powdery mildew) | on vine |
| Piricularia oryzae | (blast) | on rice |
| Plasmopara viticola | (downy mildew) | on vine |
| Venturia inaequalis | (scab) | on apple |
| Botrytis tulipae | (fire) | on bulbs |
| Nigrospora sphaerica | (squirter) | on bananas |
| Phomopsis citri | (scab) | on citrus |
| Alternaria citri | (end rot) | on citrus |
| Phytophthora citrophthora | (brown rot) | on citrus |
| Penicillium digitatum | (green mould) | on citrus |
| Gloeosporium musarum | (black end) | on bananas |
| Fusarium caeruleum | (dry rot) | on potatoes |
| Botrodiplodia theobromae | (stalk rot) | on bananas |
| Ceratocystis paradoxa | (gangrene) | on potatoes |
| Phoma exigua | (rot) | on pineapple |
| Phytophthora parasitica | (grey mould) | on citrus |
| Xanthomonas oryzae | (bacterial leaf blight) | on rice |
| Xanthomonas malyacearum | (blackarm) | on cotton |
| Erwinia amylovora | (fire blight) | on pears and apple |
| Erwinia carotovora | (bacterial soft rot) | of vegetables |
| Pseudomonas phaseolicola | (halo blight) | on beans |
| Pseudomonas syringae | (dieback) | of stone fruit |
| Pseudomonas mors-prunorum | (bacterial canker) | of stone fruit |
| Corynebacterium michinganese | (bacterial canker) | |
| Streptomyces scabies | (scab) | on potatoes |
| Agrobacterium tumefaciens | (crown gall) | |
| Fusarium culmorum | (damping off) | pea seedlings |

The compounds are also algicidal.

In use, the invention compounds, or compositions containing them, may be used to combat pests in a variety of ways. Thus the pests themselves, or the locus of the pests, or the pest habitat may be treated to control the pests.

In a further feature therefore the invention provides a method of combating pests wherein the pests, the locus of the pests, or the habitat of the pests is treated with a compound or a composition according to the invention.

The invention also provides a method of treating plants with a compound or composition according to the invention to render them less susceptible to damage by pests, which may already be occurring (i.e. treatment to eradicate an infestation or infection) or which are expected to occur (i.e. treatment to protect the plant from an infestation or infection).

In a yet further feature, therefore, the invention provides a method of treating plants to render them less susceptible to damage by pests, which comprises treating the plants, or the seeds, corms, bulbs, tubers, rhizomes or other propagative parts of the plants, with a compound or composition according to the invention.

If desired the medium in which the plants are growing may be similarly treated with a compound or composition according to the invention.

In another feature, therefore the invention provides a method of treating a medium in which plants are growing or to be grown which comprises applying to the medium a compound or composition according to the invention.

The compounds and compositions of the invention may be used for agricultural or horticultural purposes and the compound or type of composition used in any instance will depend upon the particular purposes for which it is to be used.

Compositions comprising the invention compounds may be in the form of dusting powders or granules wherein the active ingredient is mixed with a solid diluent or carrier. Suitable solid diluents or carriers may be, for example kaolinite (china clay), montmorillonite, attapulgite, talc, pumic, silica, calcium carbonate, gypsum, powdered magnesia, Fuller's earth, Hewitt's earth and diatomaceous earth. Compositions for dressing seed, for example, may comprise an agent assisting the adhesion of the composition to the seed, for example, a mineral oil.

The composition may also be in the form of dispersible powders or grains comprising, in addition to the active ingredient, a wetting agent to facilitate the dispersion of the powder or grains in liquids. Such powders or grains may include fillers, suspending agents and the like.

The compositions may also be in the form of liquid preparations to be used as dips or sprays which are generally aqueous dispersions or emulsions containing the active ingredient in the presence of one or more wetting agents, dispersing agents, emulsifying agents or suspending agents.

Wetting agents, dispersing agents and emulsifying agents may be of the cationic, anionic, or non-ionic type. Suitable agents of the cationic type include, for example, quaternary ammonium compounds, for example cetyltrimethylammonium bromide. Suitable agents of the anionic type include, for example, soaps, salts of aliphatic monoesters of sulphuric acid, for example sodium lauryl sulphate, salts of sulphonated aromatic compounds, for example sodium dodecylbenzenesulphonate, sodium calcium, or ammonium lignosulphonate, butylnaphthalene sulphonate, and a mixture of the sodium salts of diisopropyl- and triisopropylnaphthalene sulphonic acids.

Suitable agents of the non-ionic type include, for example, the condensation proucts of ethylene oxide with fatty alcohols such as oleyl alcohol or cetyl alcohol, or with alkyl phenols such as octylphenol, nonylphenol and octylcresol. Other non-ionic agents are the partial esters derived from long chain fatty acids and hexitol anhydrides, the condensation products of the said partial esters with ethylene oxide, the lecithins, and block copolymers of ethylene oxide and propylene oxide.

Suitable suspending agents are, for example, bentonite, pyrogenic silica, and hydrophilic colloids, for example polyvinylpyrrolidone and sodium carboxylmethylcellulose, and the vegetable gums, for example gum acacia and gum tragacanth.

The aqueous solutions dispersions or emulsions may be prepared by dissolving the active ingredient or ingredients in an organic solvent which may contain one or more wetting, dispersing or emulsifying agents and then adding the mixture so obtained to water which may likewise contain one or more wetting, dispersing or emulsifying agents. Suitable organic solvents are ethylene dichloride, isopropyl alcohol, propylene glycol, diacetone alcohol, toluene, kerosene, methylnaphthalene, xylenes and trichloroethylene.

The compounds of the invention may also be formulated into compositions comprising capsules or microcapsules containing either the active ingredient, and prepared by any of the known encapsulation or microencapsulation techniques.

The compositions to be used as sprays may also be in the form of aerosols wherein the formulation is held in a container under pressure in the presence of a propellant such as fluorotrichloromethane or dichlorodifluoromethane.

By the inclusion of suitable additives, for example, for improving the distribution, adhesive power and resistance to rain on treated surfaces, the different compositions can be better adapted for the various uses for which they are intended.

The compounds of this invention may also be conveniently formulated by admixing them with fetilizers. A preferred composition of this type comprises granules of fertilizer material incorporating, for example coated with, a compound of the invention. The fertilizer may, for example, comprise nitrogen or phosphate-containing substances.

In yet a further aspect of the invention, therefore, we provide a pesticidal composition comprising as an active ingredient a compound of the invention in admixture with a fertilizer material.

The compositions which are to be used in the form of aqueous dispersions or emulsions are generally supplied in the form of a concentrate containing a high proportion of the active ingredient or ingredients, the said concentrate to be diluted with water before use.

These concentrates are often required to withstand storage, to be capable of dilution with water in order to form aqueous preparations which remain homogeneous for a sufficient time to enable them to be applied by conventional spray equipment. The concentrates may conveniently contain from 10–85% by weight of the active ingredient or ingredients and generally from 25–60% by weight of the active ingredient or ingredients. When diluted to form aqueous preparations, such preparations may contain varying amounts of the active ingredient or ingredients depending upon the purpose for which they are to be used, but an aqueous preparation containing between 0.001% and 1.0% by weight of the active ingredient or ingredients may be used.

It is to be understood that the pesticidal compositions of this invention may comprise, in addition to a compound of the invention, one or more other compounds having biological activity.

The invention is illustrated, but not limited, by the following examples.

EXAMPLE 1

This example illustrates the preparation of 2,3,5,6-tetrafluoro-2',4-bistrifluoromethyl-4'-nitrodiphenylamine (Compound No. 3, Table I) having the structure:

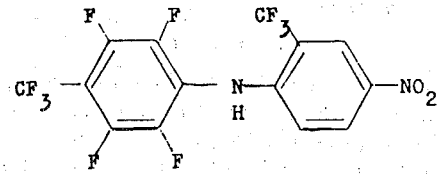

2-Amino-5-nitrobenzotrifluoride (4.0 g), in solution in dry dimethylformamide, was added with stirring to a suspension of sodium hydride (1.56 g) in dimethylformamide at 0°C. When effervescence had ceased the mixture was allowed to warm to 15°–18°C and was then stirred for 45 minutes. After recooling the mixture to 0°C, octafluorotoluene (4.58 g), in solution in dry dimethylformamide, was carefully added. When the addition was complete, the mixture was stirred for 4 hours at the ambient temperature, and then poured on to a mixture of ice, salt and water (ca. 600 ml.) Acidification of the mixture thus produced yielded a buff precipitate which was recrystallised twice from a mixture of methylene chloride and petroleum ether (boiling range 40°–60°C) to give 2,3,5,6-tetrafluoro-2',4-bistrifluoromethyl-4'-nitrodiphenylamine having a melting point of 128.5°–132.5°C. EXAMPLE 2

The procedure illustrated in Example 1 was used to prepare other invention compounds, using the appropriate reactants as set out below: 4,4'-Dinitro-2,3,5,6-tetrafluoro-2'-trifluoromethyldiphenylamine (Compound No. 1, Table I) from pentafluoronitrobenzene and 2-amino-5-nitrobenzotrifluoride.

4,4'-Dinitro-2,3,5,6-tetrachloro-2'-trifluoromethyldiphenylamine (Compound No. 2, Table I) from pentachloronitrobenzene and 2-amino-5-nitrobenzotrifluoride.

4-Bromo-4'-nitro-2,3,5,6-tetrafluoro-2'-trifluoromethyldiphenylamine (Compound No. 4, Table I) from pentafluorobromobenzene and 2-amino-5-nitrobenzotrifluoride.

3,5-Difluoro-4'-nitro-2,4,6-trichloro-2'-trifluorodiphenylamine (Compound No. 5, Table I) from 1,3,5-trichloro-2,4,6-trifluorobenzene and 2-amino-5-nitrobenzotrifluoride.

4-Methyl-4'-nitro-2,3,5,6-tetrafluoro-2'-trifluoromethyldiphenylamine (Compound No. 6, Table I) from 2,3,4,5,6-pentafluoro-toluene and 2-amino-5-nitrobenzotrifluoride.

4'-Nitro-2,3,4,5,6-pentafluoro-2'-trifluoromethyldiphenylamine (Compound No. 7, Table I) from hexafluorobenzene and 2'amino-5-nitrobenzotrifluoride.

2(2-heptafluoronaphthylamino)-5-nitrobenzotrifluoride, or the corresponding 1-heptafluoronaphthylamino isomer, (Compound No. 8, Table I) from octafluoronaphthalene and 2-amino-5-nitrobenzotrifluoride.

EXAMPLE 3

The activity of a number of the compounds were tested against a variety of insect and other invertebrate pests. The compounds were used in the form of a liquid preparation containing 0.1% by weight of the compound except in the rate with *Aedes aegypti* and *Meloidogyne incognita* where the preparations contained 0.01% by weight of the compound. The preparations were made by dissolving each of the compounds in a mixture of solvents consisting of 4 parts by volume of acetone and 1 part by volume of diacetone alcohol. The solutions were then diluted with water containing 0.01% by weight of a wetting agent sold under the trade name "LISSAPOL" NX until the liquid preparations contained the required concentration of the compound. "LISSAPOL" is a registered Trade Mark.

The test procedure adopted with regard to each pests was basically the same and comprised supporting a number of the pests on a medium which was usually a host plant or a foodstuff on which the pests feed, and treating either or both the pests and the medium with the preparations.

The mortality of the pests was then assessed at periods usually varying from one to three days after the treatment.

The results of the tests are given below in Table 2. In this table the first column indicates the name of the pest species. Each of the subsequent columns indicates the host plant or medium on which it was supported, the number of days which were allowed to elapse after the treatment before assessing the mortality of the pests, and the results obtained for each of the compounds, numbered as in Table I above. The assessment is expressed in integers which range from 0–3.

0 represents less than 30% kill
1 represents 30–49% kill
2 represents 50–90% kill
3 represents over 9% kill A dash (—) in Table 2 indicates that no test was carried out. The symbol A in Table 2 indicates that an antifeeding effect was observed.

TABLE 2

| Pest Species | Support Medium | No. of days | 1 | 2 | 3 | 4 | 5 | 6 | 7 | 8 |
|---|---|---|---|---|---|---|---|---|---|---|
| Tetranychus telarius (red spider mites, adults) | French Bean | 3 | 3 | 0 | 3 | 3 | 3 | 1 | 0 | 1 |
| Tetranychus telarius (red spider mites, eggs) | French Bean | 3 | 3 | 0 | 3 | 0 | 0 | 0 | 3 | 0 |
| Aphis fabae (green aphids) | Broad Bean | 2 | 0 | 0 | 3 | 0 | 0 | 0 | 3 | 0 |
| Megoura viceae (black aphids) | Broad Bean | 2 | 0 | 0 | 3 | 0 | 0 | 0 | 0 | 0 |
| Aedes aegypti (mosquito larvae) | Water | 1 | 3 | 3 | 3 | 3 | 3 | 0 | 0 | 0 |
| Aedes aegypti (Mosquito adults) | Plywood | 1 | 0 | 0 | 3 | 0 | 0 | 0 | 1 | 0 |
| Musca domestica (houseflies-contact test*) | Milk/Sugar | 2 | 1 | 1 | 3 | 2 | 0 | 0 | 1 | 0 |
| Musca domestica (houseflies-residual test*) | Plywood | 2 | 0 | 0 | 3 | 0 | 0 | 0 | — | — |
| Pieris brassicae (cabbage white caterpillars) | Cabbage | 2 | 0 A | 0 A | 3 A | 3 | 3 | 0 | 0 | 0 |
| Plutella maculipennis (diamond back moth, larvae) | Mustard | 2 | 0 | 3 A | 3 A | 3 A | 3 A | 0 | 3 A | 0 |
| Phaedon cochleariae (mustard beetles) | Mustard | 2 | 0 | 2 | 2 | 0 A | 1 A | 0 A | 0 | 0 |
| Calandra granaria (grain beetles) | Grain | 2 | 0 | 3 | 3 | 0 | 0 | 0 | 0 | 0 |
| Blatella germanica (cockroaches) | — | 1 | — | 2 | 3 | 0 | 0 | 0 | 0 | — |
| Tribolium confusum (four beetles) | Grain | 2 | — | — | 3 | 0 | 0 | 0 | 0 | 0 |
| Meloidogyne incognita (nematodes) | Water | 1 | — | — | — | 3 | 2 | — | 0 | — |

*In the contact test the flies are sprayed directly; in the residual test the flies are placed on a medium that had previously been treated.

EXAMPLE 4

The compounds of this invention were tested against a variety of foliar fungal diseases of plants. The technique employed is to spray the foliage of the undiseased plants with a solution of the test compound and also to drench the soil in which the plants are growing with another solution of the same test compound. All solutions for spraying and drenching contained 0.01% of the test compound. The plants were then infected with the disease it was desired to control and after a period of days, depending upon the particular disease, the extent of the disease was visually assessed. The results are given in Table 3 a below, wherein the extent of the disease is given in the form of a grading as follows:

| Grading | Percentage Amount of Disease |
|---|---|
| 0 | 61 to 100 |
| 1 | 26 to 60 |
| 2 | 6 to 25 |
| 33 | 0 to 5 |

In Table 3 the disease is gen in the first column, and in the second column is given the time which elapsed between infecting the plants and assessing the amount of disease.

TABLE 3

| Disease and Plant | Time Interval (days) | Disease Code Letter (Table 4a) |
|---|---|---|
| Puccinia recondita (wheat) | 10 | A |
| Phytophthora infestans (tomato) | 3 | B |
| Podosphaera leucotricha (apple) | 10 | C |
| Uncinula necator (vine) | 10 | D |
| Plasmopara viticola (vine) | 7 | E |
| Piricularia oryzae (rice) | 7 | F |
| Botrytis cinerea (bean) | 3 | G |

TABLE 3a

| No. of Compound Table I | Disease Code Letter (Table 3) | | | | | | |
|---|---|---|---|---|---|---|---|
| | A | B | C | D | E | F | G |
| 1 | 3 | 3 | 0 | 3 | 2 | 3 | |
| 2 | 0 | 3 | — | 3 | 3 | 2 | 2 |
| 3 | 2 | — | 3 | 3 | 3 | — | 0 |
| 4 | 0 | 0 | 0 | — | 3 | — | 0 |
| 5 | 1 | 0 | 2 | 1 | 3 | — | 0 |
| 6 | 0 | 0 | 1 | 1 | 1 | — | 1 |
| 7 | 0 | 3 | 2 | 2 | 3 | — | 0 |
| 8 | 0 | 0 | 2 | 1 | 0 | — | 0 |

The compounds were also active against apple scab, Venturia inaequalis.

EXAMPLE 5

The culture Fusarium culmorum was maintained on 2% malt agar test tube slopes at 20°C. Thirteen to seventeen days prior to testing the chemical, the culture was transferred to soil cornmeals, which consisted of 400 grams of 5% maize meal in John Innes seed compost at the rate of 2 cornmeals to 3 buckets of compost (2 gallon capacity buckets). The seeds were prepared by rolling 10 grams of wheat seeds in a 25% china clay formulation of the chemical (where the chemical was a powder) or a 12.5% china clay formulation (where the chemical was a liquid) at the rate of 1000 ppm weight/weight, e.g. 40 milligrams of 25% formulation on 10 grams of seeds. To test the chemical approximately 100 grams of the mixed soil was placed in a fibre pot, twenty seeds were placed on the surface and a further approximate 100 grams were placed on top of the seeds. This was repeated 3 times making four replicates in all. The pots were maintaned in the greenhouse between 16°C and 20°C. After 10 days the number of germinated seeds was recorded and after 17 days the roots were uncovered and the number healthy recorded. These recordings were compared with untreated seeds and seeds treated with mercury (Agrosan) and calculations were made to obtain a grading for disease control. The gradings used were the same as those of the previous Example. Compound No. 3 (Table I) gave a grading of 2.

EXAMPLE 6

The activity of the compound of the invention against a wide variety of plant bacterial diseases and fungal post-harvest saprophytic diseases was investigated by in vitro tests as follows. 5 mg. of the compound under tests was dissolved or suspended in 10 cc. of acetone and 2 cc. of this solution or suspension was added to 18 cc. of nutrient agar (for the bacterial diseases) or 16 cc. of 2% malt agar (for the fungal diseases) to give a final concentration of 50 parts per million of the compound under tests. 2 cc. of a streptomycin preparation containing 100 units/cc. was added to the malt agar to prevent bacterial contamination of the fungal tests.

The agar preparations were dried overnight in petri dishes and inoculated the following morning with the bacterial or fungal diseases using a multipoint inoculator. The antibacterial activity was assessed after 5 days and the antifungal activity after 6 days.

The results of the tests are set out below in Table 5 (antibacterial activity) and Table 6 (antifungal activity). The results are graded as in Example 4 above. The names of the disease organisms are indicated in Table 4.

TABLE 4

| Bacterial Disease Organism | Code Table 5 | Fungal Disease Organism | Code Table 6 |
|---|---|---|---|
| Agrobacterium tumifaciens | B1 | Nigrospora sphaerica | F1 |
| Gorynebacterium michiganense | B2 | Phytophthora Citrophthora | F2 |
| Erwinia carotovora | B4 | Alternaria Citri | F3 |
| Xanthomonas oryzae | B5 | Diplodia natalensis | F4 |
| Psendomonas syringae | B6 | Phomopsis citri | F5 |
| Streptomyces scabies | B7 | Ceratocystis paradoxa | F6 |
| Pseudomonas mors-prunorum | B8 | Gloeosporium musarum | F7 |
| Pseudomonas phaseolicola | B9 | Penicillium digitatum | F8 |
| Erwinia amylovora | B10 | Phoma exigua | F9 |
| | | Botrytis tulipae | F10 |
| | | Botrodiplodia theobromae | F11 |
| | | Fusarium caeruleum | F12 |

TABLE 5

| Compound No. Table I | B1 | B2 | B3 | B4 | B5 | B6 | B7 | B8 | B9 | B10 |
|---|---|---|---|---|---|---|---|---|---|---|
| 1 | 3 | 3 | 3 | 3 | 3 | 3 | 3 | 3 | 3 | 3 |
| 2 | 1 | 2 | 0 | 1 | 2 | 2 | 3 | 0 | 0 | 0 |
| 3 | 0 | 2 | 0 | 2 | 0 | 2 | 0 | 0 | 0 | |

TABLE 6

| Compound No. Table I | F1 | F2 | F3 | F4 | F5 | F6 | F7 | F8 | F9 | F10 | F11 | F12 |
|---|---|---|---|---|---|---|---|---|---|---|---|---|
| 1 | 3 | 3 | 3 | 3 | 3 | 3 | 3 | 3 | 3 | 3 | 3 | 3 |
| 2 | 3 | 3 | 3 | 3 | 3 | 0 | 3 | 3 | 0 | 3 | 3 | 1 |
| 3 | 2 | 2 | 2 | 2 | 2 | 0 | 2 | 2 | 2 | 2 | 2 | 2 |

EXAMPLE 7

Compounds of the invention were tested as potential algicides. A mixed algal culture was treated with a quantity of an aqueous suspension of the compound under test so that the culture contained 20 parts per million of the compound. Compound No. 2 (Table I) was found to completely control the algal growth at this concentration.

The following Examples illustrate pesticidal compositions according to the invention.

EXAMPLE 8

This Example illustrates a concentrate comprising a miscible oil which is readily convertible by dilution with water into a liquid preparation suitable for spraying purposes.

The concentrate has the following compositions:

| | % wt. |
|---|---|
| Compound No. 1 of Table I | 25.0 |
| 'LUBROL' L (alkylphenol/ethylene oxide condensate; 'Lubrol' is a Trade Mark) | 2.5 |
| Calcium dodecylbenzenesulphonate | 2.5 |
| 'AROMASOL' H (alkylbenzene solvent; 'Aromasol' is a Trade Mark) | 70.0 |
| | 100.0 |

EXAMPLE 9

This Example also illustrates a concentrate which is in the form of a miscible oil. The composition of this concentrate is as follows:

| | % wt. |
|---|---|
| Compound No. 2 of Table I | 25.0 |
| 'LUBROL' L ('Lubrol' is a Trade Mark) | 4.0 |
| Calcium dodecylbenzenesulphonate | 6.0 |
| 'AROMASOL' H ('Aromasol' is a Trade Mark) | 65.0 |
| | 100.0 |

EXAMPLE 10

This Example illustrates a wettable powder having the following composition:

| | % wt. |
|---|---|
| Compound No. 3 of Table I | 25.0 |
| Sodium silicate | 5.0 |
| Calcium lignosulphonate | 5.0 |
| China clay | 65.0 |
| | 100.0 |

EXAMPLE 11

This Example illustrates an atomisable fluid comprising a mixture consisting of 25% by weight of the compound No. 1 of Table I and 75% by weight of xylene.

EXAMPLE 12

This Example illustrates a dusting powder which may be applied directly to plants or other surfaces and comprises 1% by weight of Compound No. 2 of Table I and 99% by weight of talc.

EXAMPLE 13

25 Parts by weight of compound No. of Table I, 65 parts by weight of xylene, and 10 parts of an alkyl aryl polyether alcohol 'Triton' X-100 ('Triton' is a Trade Mark) were mixed. There was thus obtained an emulsion concentrate which can be mixed with water to produce an emulsion suitable for use in agricultural applications.

EXAMPLE 14

5 Parts by weight of Compound No. 1 of Table I were thoroughly mixed in a suitable mixer with 95 parts by weight of talc. There was thus obtained a dusting powder.

EXAMPLE 15

10 Parts by weight of Compound No. 7 of Table I, 10 Parts of an ethylene oxide-octylphenol condensate ("Lissapol" NX; "Lissapol" is a Trade Mark) and 80 parts by weight of diacetone alcohol were thoroughly mixed. There was thus obtained a concentrate which, on mixing with water, gave an aqueous dispersion suitable for application as a spray in the control of insect pests.

EXAMPLE 16

This Example illustrates a concentrated liquid formulation in the form of an emulsion. The ingredients listed below were mixed together in the stated proportions and the whole stirred until the constituents were dissolved.

| | % wt. |
|---|---|
| Compound No. 5 of Table I | 20 |
| 'LUBROL' L ('Lubrol' is a Trade Mark) | 17 |
| Calcium dodecylbenzenesulphonate | 3 |
| Ethylene dichloride | 45 |
| 'AROMASOL' H ('Aromasol' is a Trade Mark) | 15 |
| | 100 |

EXAMPLE 17

The ingredients listed below were ground together in the proportions stated to produce a powdered mixture readily dispersible in liquids.

| | % wt. |
|---|---|
| Compound No. 1 of Table 1 | 50 |
| 'Dispersol' T ('Dispersol' is a Trade Mark) | 5 |
| China Clay | 45 |
| | 100 |

EXAMPLE 18

A composition in the form of grains readily dispersible in a liquid (for example water) was prepared by grindng together the first four of the ingredients listed below in the presence of water and then the sodium acetate was mixed in.

The admixture was dried and passed through a British Standard mesh sieve, size 44–100 to obtain the desired size of grains.

| | % wt. |
|---|---|
| Compound No. 2 of Table I | 50 |
| 'Dispersol' ('Dispersol' is a Trade Mark) | 12.5 |
| Calcium lignosulphonate | 5 |
| Calcium dodecylbenzenesulphonate | 12.5 |
| Sodium acetate | 20 |
| | 100 |

EXAMPLE 19

A composition suitable for use as a seed dressing was prepared by mixing all three of the ingredient set out below in the proportions stated.

| | % wt. |
|---|---|
| Compound No. 1 of Table I | 80 |
| Mineral Oil | 2 |
| China Clay | 18 |
| | 100 |

EXAMPLE 20

A composition suitable for use as a seed dressing was prepared by mixing all three of the ingredients set out below in the proportions stated.

| | % wt. |
|---|---|
| Compound No. 2 of Table I | 80 |
| Mineral Oil | 2 |
| China Clay | 18 |
| | 100 |

EXAMPLE 21

A granular compositions was prepared by dissolving the active ingredient in a solvent, spraying the solution obtained on to granules of pumice and allowing the solvent to evaporate.

| | % wt. |
|---|---|
| Compound No. 2 of Table I | 5 |
| Pumice Granules | 95 |
| | 100 |

EXAMPLE 22

An aqueous dispersion formulation was prepared by mixing and grinding the ingredients recited below in the proportions stated.

| | % wt. |
|---|---|
| Compound No. 3 of Table I | 40 |
| Calcium lignosulphonate | 10 |
| Water | 50 |
| | 100 |

The following constitutes an explanation of the compositions or substances represented by the various Trade Marks and Trade Names referred to in the foregoing Examples.

| | |
|---|---|
| 'LUBROL' L | is a condensate of 1 mole of nonyl phenol with 13 molar proportions of ethylene oxide. |
| 'AROMASOL' H | is a solvent mixture of alkylbenzenes. |
| 'DISPERSOL' T | is a mixture of sodium sulphate and a condensate of formaldehyde with the sodium salt of naphthalene sulphonic acid. |
| 'LISSAPOL' NX | is a condensate of 1 mole of nonyl phenol with 8 moles of ethylene oxide. |

We claim:
1. A compound of the formula:

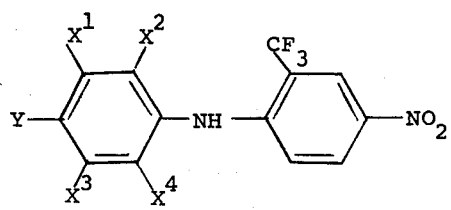

wherein $X^1$, $X^2$, $X^3$ and $X^4$, which may be the same or different, are halogen atoms, and Y is halogen, trifluoromethyl or nitro.

2. A compound of the formula:

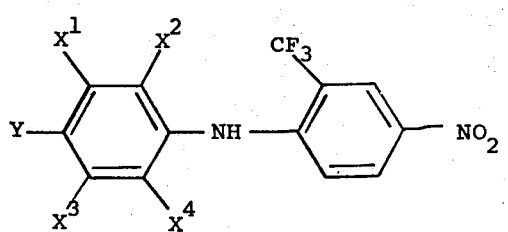

wherein $X^1$, $X^2$, $X^3$ and $X^4$, which may be the same or different, are halogen atoms, and Y is halogen.

3. A compound of the formula:

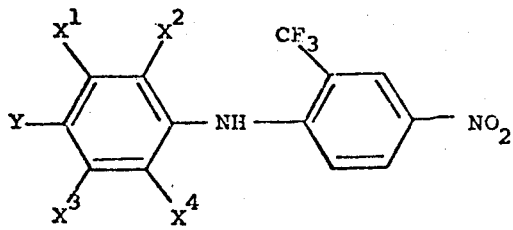

wherein $X^1$, $X^2$, $X^3$ and $X^4$, which may be the same or different, are halogen atoms, and Y is trifluoromethyl.

4. A compound of the formula:

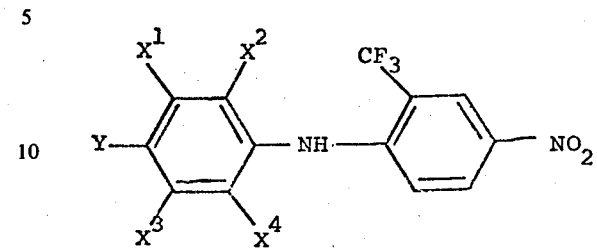

wherein $X^1$, $X^2$, $X^3$ and $X^4$, which may be the same or different, are halogen atoms, and Y is nitro.

5. A compound of the formula:

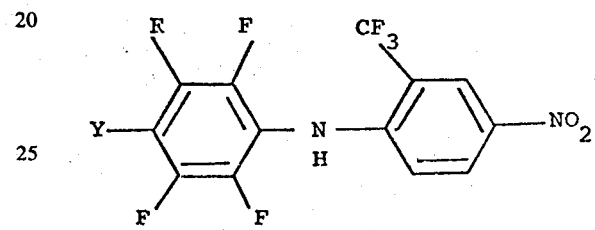

wherein Y is trifluoromethyl.

6. A compound of the formula:

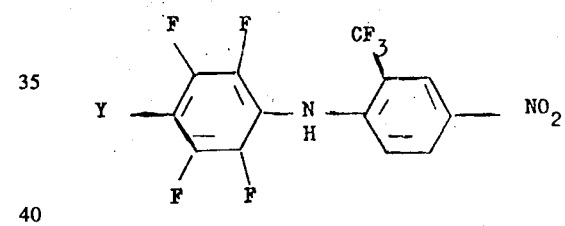

wherein Y is fluorine, trifluoromethyl or nitro.

* * * * *